(12) United States Patent
Kawamura et al.

(10) Patent No.: US 9,580,376 B2
(45) Date of Patent: Feb. 28, 2017

(54) METHOD FOR PRODUCING UNSATURATED ALDEHYDE AND/OR UNSATURATED CARBOXYLIC ACID

(71) Applicant: Nippon Kayaku Kabushiki Kaisha, Tokyo (JP)

(72) Inventors: Tomoyuki Kawamura, Yamaguchi (JP); Tatsuhiko Kurakami, Yamaguchi (JP); Yuuta Nakazawa, Yamaguchi (JP); Toru Kawaguchi, Yamaguchi (JP); Motohiko Sugiyama, Yamaguchi (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/903,410

(22) PCT Filed: Jul. 17, 2014

(86) PCT No.: PCT/JP2014/068992
§ 371 (c)(1),
(2) Date: Jan. 7, 2016

(87) PCT Pub. No.: WO2015/008814
PCT Pub. Date: Jan. 22, 2015

(65) Prior Publication Data
US 2016/0145180 A1    May 26, 2016

(30) Foreign Application Priority Data
Jul. 18, 2013    (JP) .................................. 2013-149333

(51) Int. Cl.
| | | |
|---|---|---|
| *C07C 45/27* | (2006.01) | |
| *C07C 51/00* | (2006.01) | |
| *C07C 51/16* | (2006.01) | |
| *C07C 45/35* | (2006.01) | |
| *C07C 51/25* | (2006.01) | |
| *B01J 35/00* | (2006.01) | |
| *B01J 23/00* | (2006.01) | |
| *B01J 37/00* | (2006.01) | |
| *B01J 23/887* | (2006.01) | |
| *B01J 37/03* | (2006.01) | |

(52) U.S. Cl.
CPC ............. *C07C 51/16* (2013.01); *B01J 23/002* (2013.01); *B01J 23/8876* (2013.01); *B01J 35/0006* (2013.01); *B01J 37/0018* (2013.01); *B01J 37/0045* (2013.01); *C07C 45/27* (2013.01); *C07C 45/35* (2013.01); *C07C 51/252* (2013.01); *B01J 37/031* (2013.01); *B01J 2523/00* (2013.01)

(58) Field of Classification Search
CPC ....... C07C 51/16; C07C 51/252; C07C 45/27; C07C 45/35; B01J 37/00; B01J 23/00

USPC .......................................... 568/449; 562/542
See application file for complete search history.

(56) References Cited

U.S. PATENT DOCUMENTS

| | | | |
|---|---|---|---|
| 5,731,689 | A | 3/1998 | Sato |
| 6,399,818 | B2 | 6/2002 | Tanimoto et al. |
| 6,620,968 | B1 | 9/2003 | Lonzetta et al. |
| 6,781,013 | B2 | 8/2004 | Tanimoto |
| 6,960,684 | B2 | 11/2005 | Yunoki |
| 7,161,044 | B2 | 1/2007 | Nakamura et al. |
| 8,969,618 | B2 | 3/2015 | Kurakami et al. |
| 2004/0059155 | A1 | 3/2004 | Lonzetta et al. |
| 2010/0036157 | A1 | 2/2010 | Ko et al. |
| 2013/0023699 | A1 | 1/2013 | Macht et al. |

FOREIGN PATENT DOCUMENTS

| | | |
|---|---|---|
| CN | 1255366 C | 5/2006 |
| CN | 1305827 C | 3/2007 |
| CN | 101657408 A | 2/2010 |
| EP | 1125911 A2 | 8/2001 |
| EP | 1526123 A1 | 4/2005 |
| EP | 2671862 A1 | 12/2013 |
| JP | 8-3093 A | 1/1996 |
| JP | 8-336298 A | 12/1996 |
| JP | 2001-213821 A | 8/2001 |
| JP | 2001-226302 A | 8/2001 |
| JP | 2001-328951 A | 11/2001 |
| JP | 2004-2209 A | 1/2004 |
| JP | 2005-162744 A | 6/2005 |
| JP | 2005-213179 A | 8/2005 |
| JP | 2005-320315 A | 11/2005 |
| JP | 2007-326787 A | 12/2007 |
| JP | 2012-176938 A | 9/2012 |

(Continued)

OTHER PUBLICATIONS

Japanese communication, with English translation, dated Apr. 12, 2016 in corresponding Japanese patent application No. 2015-527327.

(Continued)

*Primary Examiner* — Sikarl Witherspoon
(74) *Attorney, Agent, or Firm* — Nields, Lemack & Frame, LLC

(57) ABSTRACT

Provided is a method of subjecting an alkene to partial oxidation by using a fixed bed multitubular reactor, thereby producing an unsaturated aldehyde and/or an unsaturated carboxylic acid each corresponding to the alkene, wherein a plurality of catalyst layers formed by N division (N is N≥2) with respect to a gas flow direction of a reaction tube are provided, and when a change (° C.) of hot spot temperature per 1° C. change of reaction bath temperature in the catalyst layer is designated as Sn, at least one of the plurality of catalyst layers is regulated to Sn≤6.

15 Claims, No Drawings

(56) References Cited

FOREIGN PATENT DOCUMENTS

| JP | 2014-019675 A | 2/2014 |
|----|---------------|--------|
| JP | 2014-523809 A | 9/2014 |

OTHER PUBLICATIONS

International Search Report and Written Opinion mailed Sep. 30, 2014 in corresponding PCT application No. PCT/JP2014/068992.
Taiwanese communication, with English translation, dated Jan. 22, 2016 in corresponding Taiwanese patent application No. 103124805.
Chinese communication, with English translation, dated Jul. 12, 2016 in corresponding Chinese patent application No. 201480040828.8.
Japanese communication, with English translation, dated Nov. 22, 2016 in corresponding Japanese patent application No. 2015-527327.
European communication dated Nov. 25, 2016 in corresponding European patent application No. 14825697.7.

METHOD FOR PRODUCING UNSATURATED ALDEHYDE AND/OR UNSATURATED CARBOXYLIC ACID

TECHNICAL FIELD

The present invention relates to a method of subjecting an alkene to gas-phase catalytic oxidation in the presence of molecular oxygen or a molecular oxygen-containing gas, thereby producing an unsaturated aldehyde and/or an unsaturated carboxylic acid each corresponding to the alkene.

BACKGROUND ART

Although a method of using, as a raw material, an alkene or an alcohol capable of producing an alkene through its intramolecular dehydration reaction, thereby producing a corresponding unsaturated aldehyde or unsaturated carboxylic acid is widely carried out on an industrial scale, the generation of a local high-temperature portion (hot spot) in a catalyst layer is of a serious problem. The generation of a hot spot leads to shortening of a catalyst life, lowering of the yield to be caused due to an excessive oxidation reaction, and in the worst case, a runaway reaction, and therefore, there are made some proposals regarding a technology of controlling the activity of a catalyst to be filled in a portion where the hot spot is generated in order to suppress the hot spot temperature. For example, Patent Document 1 discloses a technology of decreasing the hot spot temperature by using a catalyst whose activity is adjusted by varying the supporting amount or using a catalyst whose activity is adjusted by varying the calcination temperature of the catalyst. Patent Document 2 discloses a technology of using a catalyst whose activity is adjusted by varying a ratio of the apparent density of the catalyst. Patent Document 3 discloses a technology of using a catalyst whose activity is adjusted by not only varying the content of an inert component of the shaped catalyst but also varying the occupation volume of the shaped catalyst, the kind and/or amount of the alkali metal, and the calcination temperature of the catalyst. Patent Document 4 discloses a technology of providing reaction zones in which the occupation volume of the shaped catalyst is varied and mixing an inert substance in at least one reaction zone. Patent Document 5 discloses a technology of using a catalyst whose activity is adjusted by varying the calcination temperature of the catalyst. Patent Document 6 discloses a technology of using a catalyst whose activity is adjusted by varying the occupation volume of the catalyst, the calcination temperature, and/or the kind or amount of the alkali metal.

BACKGROUND ART DOCUMENT

Patent Document

Patent Document 1: JP-A-H8-336298
Patent Document 2: JP-A-2004-002209
Patent Document 3: JP-A-2001-328951
Patent Document 4: JP-A-2005-320315
Patent Document 5: JP-A-HS-3093
Patent Document 6: JP-A-2001-226302

SUMMARY OF INVENTION

Problem That Invention Is To Solve

However, even if it is contemplated to suppress the hot spot temperature by the above-described means, the effect is not sufficient yet. Furthermore, there may be involved such a problem that the catalytic performance and catalyst life expected in the industrial plant are not always obtained, and thus, an improvement was desired. For example, in the industrial plant, there may be the case where scattering in heat removal capability to be originated in a reactor structure, heat medium temperature distribution in the horizontal direction or vertical direction, or gas flow rate distribution in every reaction tube is generated. Thus, it is substantially impossible for the catalyst to be used in the same state within all of the reaction tubes. For this reason, there is demanded a technology of suppressing an increase rate of the hot spot temperature in the case where the reaction bath temperature increases. The present inventors analyzed catalysts used in the industrial plant. As a result, a reaction tube in which the catalysts in a raw material gas inlet portion are concentratedly deteriorated, a reaction tube in which the catalysts are gently deteriorated over the whole, and furthermore, astonishingly a reaction tube in which the catalysts in a raw material gas outlet portion is more deteriorated than those in an inlet portion were seen. This suggests a possibility that the hot spot temperature of the catalyst layer on the raw material gas outlet side was abnormally high, and in the worst case, there is a danger of causing a runaway reaction. This is expected to be caused due to the matter that the conversion of a raw material hydrocarbon was different, and the shape of temperature distribution was different by scattering in reaction tube diameter, scattering in heat removal capability to be originated in a reactor structure, heat medium temperature distribution in the horizontal direction or vertical direction, or gas flow rate distribution in every reaction tube in the industrial plant as described above. That is, even in the case where the reaction bath temperature fluctuated in the industrial plant, development of a technology of making it possible to keep a high yield more safely and stably over a long period of time was mentioned as a problem.

With respect to the foregoing problem, the present applicant made proposals, such as JP-A-2014-19675, etc., and contemplated to improve it. However, as a result of further extensive and intensive investigations, by regulating a change Sn of the hot spot temperature relative to a change of the reaction bath temperature to a specified value or less, there has been accomplished the present invention in which the problem that may be said to be inherent to the industrial plant as described above can be solved, and a high yield can be kept safely and stably over a long period of time.

Means for Solving Problem

Specifically, the present invention is concerned with the following.

A) A method for producing an unsaturated aldehyde and/or an unsaturated carboxylic acid, which is a method for producing an unsaturated aldehyde and/or an unsaturated carboxylic acid each corresponding to an alkene by partially oxidizing the alkene using a fixed bed multitubular reactor,
wherein a plurality of catalyst layers formed by N division (N is N≥2) with respect to a gas flow direction of a reaction tube are provided, and
when a change (° C.) of hot spot temperature per 1° C. change of reaction bath temperature in the catalyst layer is designated as Sn, at least one of the plurality of catalyst layers is regulated to Sn≤6.

B) The method for producing an unsaturated aldehyde and/or an unsaturated carboxylic acid as set forth in A), wherein at least one of the plurality of catalyst layers is regulated to Sn≤3.

C) The method for producing an unsaturated aldehyde and/or an unsaturated carboxylic acid as set forth in A) or B), wherein N is 2 or 3.

D) The method for producing an unsaturated aldehyde and/or an unsaturated carboxylic acid as set forth in any one of A) to C), wherein a concentration of the alkene in a raw material is 7 to 12% by volume.

E) The method for producing an unsaturated aldehyde and/or an unsaturated carboxylic acid as set forth in any one of A) to D), wherein all of the catalyst layers contain a complex metal oxide having a formulation represented by the following formula (1):

    Formula (1)

(X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), arsenic (As), antimony (Sb) and tungsten (W); Z is at least one element selected from the group consisting of sodium (Na), potassium (K), rubidium (Rb) and cesium (Cs); a to g represent atomic ratios of the respective components; h is a numerical value determined by degrees of oxidations of the catalyst components; a=0.80 to 2.0, b=1 to 3; c=3 to 7; d=2 to 4; e=0 to 10; f=0 to 10; g=0.01 to 0.10; h is expressed by the numerical value satisfying the oxidation states of other elements; d/a is 1.9 or more and 3.2 or less; d/g is 29 or more and 69 or less; and a/g is 18 or more and 39 or less.)

Effects of Invention

According to the present invention, in using, as a raw material, an alkene or an alcohol capable of producing an alkene through its intramolecular dehydration reaction to produce a corresponding unsaturated aldehyde or unsaturated carboxylic acid, it becomes possible to keep a high yield safely and stably over a long period of time even in the industrial plant.

Mode for Carrying Out Invention

In the present invention, in partially oxidizing an alkene using a fixed bed multitubular reactor, thereby producing an unsaturated aldehyde and/or an unsaturated carboxyl acid each corresponding to the alkene, a catalyst is filled in such a manner that a plurality of catalyst layers formed by N division (N is N≥2) with respect to a gas flow direction of a reaction tube are provided, and when a change (° C.) of hot spot temperature per 1° C. change of reaction bath temperature in the catalyst layer is designated as Sn, at least one of the plurality of catalyst layers is regulated to Sn≤6. Although the catalyst which is used in the present invention is not particularly limited with respect to its shape or kind so long as the above-described requirements can be met, for example, it can be prepared through the following steps.

Step a): Preparation

In general, starting raw materials of respective elements constituting the catalyst are not particularly restricted. As the molybdenum component raw material, molybdenum oxides, such as molybdenum trioxide; molybdic acids or salts thereof, such as molybdic acid and an ammonium molybdate, heteropoly acids or salts thereof, such as phosphomolybdic acid and silicomolybdic acid; and the like can be used. Preferably, in the case of using an ammonium molybdate, a high-performance catalyst can be obtained. In particular, the ammonium molybdate includes plural kinds of compounds, such as ammonium dimolybdate, ammonium tetramolybdate, ammonium heptamolybdate, etc., and among those, the case of using ammonium heptamolybdate is the most preferred. As the bismuth component raw material, bismuth salts, such as bismuth nitrate, bismuth subcarbonate, bismuth sulfate, bismuth acetate, etc.; bismuth trioxide; metallic bismuth; and the like can be used. Among those, bismuth nitrate is more preferred, and in the case of using this, a high-performance catalyst is obtained. As for raw materials of iron, cobalt, nickel and other elements, oxides, or nitrates, carbonates, organic acid salts, hydroxides and the like, each of which can become an oxide upon ignition, or mixtures thereof can be generally used. For example, the iron component raw material and the cobalt component raw material and/or the nickel component raw material are dissolved in a prescribed ratio in water and mixed under a condition at 10 to 80° C.; the mixture is mixed with an aqueous solution or slurry of the separately prepared molybdenum component raw material and Z component raw material under a condition at 20 to 90° C.; after heating and stirring the resulting mixture for about 1 hour under a condition at 20 to 90° C., an aqueous solution having the bismuth component raw material dissolved therein and optionally the X component raw material and the Y component raw material are added, thereby obtaining an aqueous solution or slurry containing the catalyst components. The both are hereinafter collectively called "liquid preparation (A)". Here, the liquid preparation (A) is not always required to contain all of the catalyst constituent elements, and a part of those elements or a part of the amounts thereof may be added in the sequent step or steps. In addition, on the occasion of preparing the liquid preparation (A), when the amount of water for dissolving each of the component raw materials, or in the case of adding an acid, such as sulfuric acid, nitric acid, hydrochloric acid, tartaric acid, acetic acid, etc., for the purpose of dissolution, the acid concentration in the aqueous solution sufficient for dissolving the raw materials is not suitable for the preparation within the range of, for example, 5% by weight to 99% by weight, there may be the case where the form of the liquid preparation (A) becomes a clay-like lump. In this case, an excellent catalyst is not obtained. The form of the liquid preparation (A) is preferably an aqueous solution or slurry because an excellent catalyst is obtained.

Step b): Drying

Subsequently, the liquid preparation (A) obtained above is dried to form a dry powder. The drying method is not particularly limited so long as it is a method capable of completely drying the liquid preparation (A); however, examples thereof include drum drying, freeze drying, spray drying, evaporation to dryness, and the like. Of these, spray drying in which the slurry can be dried into a powder or granule within a short period of time is especially preferred in the present invention. Although the drying temperature of spray drying varies depending upon the concentration of slurry, the liquid sending speed, or the like, it is approximately 70 to 150° C. in terms of a temperature at the outlet of a drying machine. In addition, it is preferred to perform drying such that an average particle diameter of the dry powder obtained on that occasion is 10 to 700 μm. There is thus obtained a dry powder (B).

Step c): Preliminary Calcination

When the obtained dry powder (B) is calcined under air circulation at 200° C. to 600° C., and preferably 300° C. to 600° C., shaping properties, mechanical strength and catalytic performance of the resulting catalyst tend to be improved. A calcination time is preferably 1 hour to 12 hours. There is thus obtained a preliminarily calcined powder (C).

Step d): Shaping

Although the shaping method is not particularly limited, on the occasion of shaping in a cylindrical or annular form, a method using a tablet shaping machine, an extrusion shaping machine, or the like is preferred. The case of shaping in a spherical form is more preferred, and the preliminarily calcined powder (C) may be shaped in a spherical form by using a shaping machine; however, a method of supporting the preliminarily calcined powder (C) (including a shaping auxiliary agent and a strength improver, if desired) on a carrier, such as an inert ceramic, etc., is preferred. Here, as for the supporting method, a tumbling granulation method, a method using a centrifugal flow coating apparatus, a wash coating method, and the like are widely known, and the supporting method is not particularly limited so long as it is a method capable of uniformly supporting the preliminarily calcined powder (C) on the carrier. However, in the case of taking into account the production efficiency of the catalyst or the performance of the prepared catalyst, more preferably, a method in which using an apparatus having a flat or uneven disk in a bottom of a fixed cylindrical vessel, a carrier charged within the vessel is vigorously agitated by means of repetition of rotation motion and revolution motion of the disk itself by rotating the disk at a high speed, and the preliminarily calcined powder (C) and optionally a shaping auxiliary agent and/or a strength improver are added thereto, thereby supporting the powder components on the carrier is preferred. It is to be noted that on the occasion of supporting, it is preferred to use a binder. Specific examples of the binder which may be used include water, ethanol, methanol, propanol, a polyhydric alcohol, polyvinyl alcohol of a polymer-based binder, a silica sol aqueous solution of an inorganic binder, and the like; ethanol, methanol, propanol and a polyhydric alcohol are preferred; and a diol, such as ethylene glycol, etc., a triol, such as glycerin, etc., and the like are more preferred. By using an appropriate amount of a glycerin aqueous solution, the shaping properties become good, and a high-performance catalyst having high mechanical strength is obtained. Specifically, in the case of using an aqueous solution having a glycerin concentration of 5% by weight or more, a catalyst having an especially high performance is obtained. The use amount of such a binder is generally 2 to 80 parts by weight based on 100 parts by weight of the preliminarily calcined powder (C). As for the inert carrier, a carrier having a diameter of about 2 to 8 mm is generally used, and the preliminarily calcined powder (C) is supported thereon. Its supporting rate is determined taking into account a catalyst use condition, for example, a reaction condition, such as a space velocity of the reaction raw materials, raw material concentrations, or the like, and it is generally 20% by weight to 80% by weight. Here, the supporting rate is expressed according to the following formula.

Supporting rate (% by weight)=100×[(Weight of preliminarily calcined powder (C) used for shaping)/{(Weight of preliminarily calcined powder (C) used for shaping)+(Weight of inert carrier used for shaping)}]     Formula (2)

There is thus obtained a shaped body (D). The mechanical strength of the shaped body (D) is also largely influenced by the atomic ratio of the catalyst formulation. That is, the mechanical strength of the shaped body (D) is influenced by the kind of a compound to be formed by regulating the atomic ratios, or the matter that even in the same compound, the phase form of a crystal structure is different. In addition, the diameter of the complex metal oxide particle formed in the preparation step or drying step or the geometric structure of the particle, and the coagulation form thereof change, and therefore, the mechanical strength of the shaped body (D) is also influenced by changes in micro physical properties, such as strength of the compound crystal in the complex metal oxide, or macro physical properties, for example, the particle size distribution of the preliminarily calcined powder. Overall physical properties including not only the preparation method of each step but also the influence of the atomic ratios determine the mechanical strength of the ultimately prepared catalyst.

Step e): Full-scale Calcination

By calcining the shaped body (D) at a temperature of 200 to 600° C. for about 1 to 12 hours, its catalytic activity and effective yield tend to be improved. The calcination temperature is preferably 400° C. or higher and 600° C. or lower, and more preferably 500° C. or higher and 600° C. or lower. Air is simple and easy and preferred as the gas to be circulated; however, besides, it is also possible to use nitrogen or carbon dioxide as an inert gas, or a nitrogen oxide-containing gas, an ammonia-containing gas, a hydrogen gas, or a mixture thereof for the purpose of rendering the system into a reducing atmosphere. There is thus obtained a catalyst (E).

Although the catalyst contained in all of the catalyst layers of the fixed bed multitubular reactor which is used for the method of the present invention is not particularly limited, a catalyst containing a complex metal oxide having a formulation represented by the following formula (1) is preferred.

$$Mo_{12}Bi_aFe_bCo_cNi_dX_eY_fZ_gO_h \quad (1)$$

(X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), arsenic (As), antimony (Sb) and tungsten (W); Z is at least one element selected from the group consisting of sodium (Na), potassium (K), rubidium (Rb) and cesium (Cs); (a) to (g) represent atomic ratios of the respective components; h is a numerical value determined by degrees of oxidations of the catalyst components; a=0.80 to 2.0, b=1 to 3; c=3 to 7; d=2 to 4; e=0 to 10; f=0 to 10; g=0.01 to 0.10; h is expressed by the numerical value satisfying the oxidation states of other elements; d/a is 1.9 or more and 3.2 or less; d/g is 29 or more and 69 or less; and a/g is 18 or more and 39 or less.)

In the complex metal oxide having the formulation represented by the foregoing formula (1), more preferably, b=1 to 2.5, d=2 to 3.5, and a/g is 18 or more and 35 or less.

The catalytic gas-phase oxidation reaction of an alkene in the present invention is carried out by introducing a mixed gas composed of 7 to 12% by volume of an alkene, 5 to 18% by volume of molecular oxygen, 0 to 60% by volume of steam, and 20 to 70% by volume of an inert gas, for example, nitrogen, carbon dioxide, etc., in terms of a raw material gas formulation onto the catalyst prepared above at a temperature ranging from 250 to 450° C. under a pressure of atmospheric pressure to 10 atms, preferably atmospheric pressure to 5 atms, and more preferably atmospheric pressure to 3 atms for a contact time of 0.5 to 10 seconds. It is to be noted that the alkene as referred to in the present invention also includes an alcohol capable of producing an alkene in its intramolecular dehydration reaction, for example, tertiary butanol. From the standpoint of production efficiency, it is preferred that a space velocity of the reaction substrate, such as an alkene, etc., to the catalyst volume [(reaction substrate feed rate (NL/hr))/(catalyst filling space volume (L))] is higher. However, when the space velocity is excessively high, from the standpoints that there may be case where the yield of a target product (acrolein+acrylic acid) is lowered; the catalyst life is shortened; and the like, the space velocity is actually in the range of preferably 40 to 200 $hr^{-1}$, and more preferably 60 to 180 $hr^{-1}$. Here, NL represents a volume in the standard state of the reaction substrate. In addition, the conversion of the alkene is preferably one in the neighborhood of the conversion at which the effective yield ((acrolein yield)+(acrylic acid yield)) is obtained, and it is generally 90 to 99.9%, preferably 96 to 99.5%, and more preferably 97.5 to 99%.

In the present invention, it is preferred that a plurality of catalyst layers formed by N division with respect to a gas flow direction of a reaction tube are provided, and the above-described plural kinds of catalysts are arranged such that the activity becomes higher from the raw material inlet part toward the outlet part in the raw material gas flow direction. Although the division number N is not particularly limited, it is generally 2 to 5, and preferably 2 to 3.

In the case where Sn becomes large, the hot spot temperature largely fluctuates relative to a change of the reaction bath temperature, resulting in the generation of a lot of demerits. First of all, the matter that the temperature of the hot spot of the catalyst layer becomes excessively high causes local deterioration of the catalyst. In addition, when the temperature of the hot spot becomes high, an excessive oxidation reaction is advanced, so that the raw materials and the target product and so on are decomposed, resulting in a lowering of the yield. Furthermore, the temperature distribution largely fluctuates, so that even a runaway reaction could be caused.

In addition, in the industrial plant, even in the case where the reaction bath temperature is not varied intentionally, there may be the case where the reaction bath temperature slightly fluctuates by an influence of an external factor. In such case, in a catalyst having large Sn, the hot spot temperature is liable to be varied, and therefore, it is necessary to pay the closest attention to the operation. Examples of the external factor include a change of the flow rate of the heat medium to be fed into a reaction bath jacket of the reactor, a fluctuation of the raw material gas flow amount due to a change of the ambient temperature, and the like.

The present invention is characterized in that a proportion of the temperature change of the hot spot of the catalyst layer is controlled within a specified range. That is, when a change (° C.) of the hot spot temperature per 1° C. change of the reaction bath temperature in the catalyst layer is designated as Sn, Sn is Sn≤6, and preferably Sn≤3. It is to be noted that Sn is 0≤Sn.

It is to be noted that the hot spot as referred to in the present invention means a maximum value of the temperature within the catalyst layer, and in general, it refers to a hot spot within the catalyst layer arranged nearest to the raw material gas inlet side. For example, in the case where no maximum value of the temperature is present in the catalyst layer arranged nearest to the raw material gas inlet side, Sn is defined while setting a maximum value of the temperature as a hot spot within the catalyst layer arranged nearest to the raw material gas inlet side in the next or subsequent layer.

Although the alkene concentration is preferably 7 to 12% by volume, when the alkene concentration is larger, Sn tends to become larger. For that reason, in the case where the alkene concentration is 8% by volume or more, the effects of the present invention are more remarkably exhibited.

In the industrial plant, by carrying out the production method as described above, the temperature sensitivity can be reduced, it makes it possible to operate the industrial plant stably over a long period of time, and a stable yield is obtained. This effect is caused due to the fact that by reducing the temperature sensitivity, a change amount of the hot spot relative to the change of the reaction bath temperature is suppressed small, so that a load of thermal deterioration in the catalyst is lightened.

EXAMPLES

Examples are hereunder described by reference to specific examples, but it should be construed that the present invention is not limited to these Examples so long as the gist of the present invention is not deviated.

It is to be noted that in the following, definitions of acrolein yield, acrylic acid yield, and effective yield are as follows.

$$\text{Acrolein yield (mol\%)} = \{(\text{Molar number of produced acrolein})/(\text{Molar number of fed propylene})\} \times 100$$

$$\text{Acrylic acid yield (mol \%)} = \{(\text{Molar number of produced acrylic acid})/(\text{Molar number of fed propylene})\} \times 100$$

$$\text{Effective yield (mol \%)} = (\text{Acrolein yield}) + (\text{Acrylic acid yield})$$

Sn as referred to in the present invention refers to a change rate of the hot spot temperature of the catalyst layer relative to the reaction bath. In particular, as for the definition thereof, Sn refers to a change (° C.) of the hot spot temperature of the catalyst relative to the 1° C. change of the reaction bath temperature. This index may also be taken as sensitivity of the hot spot temperature relative to the change of the reaction bath temperature. Thus, the present inventors call this index as the temperature sensitivity, and this can be used as an index for stability of the catalyst in operating the industrial plant using this catalyst.

As described above, Sn can be determined from the hot spot temperatures in the reaction bath temperature at two or more spots selected from arbitrary reaction bath temperatures. The reaction bath temperature for determining Sn is generally 250° C. or higher and 400° C. or lower, preferably 270° C. or higher and 380° C. or lower, and more preferably 290° C. or higher and 360° C. or lower. As a matter of course, these reaction bath temperatures should be a reaction bath temperature at which a suitable conversion of the raw material alkene is attained in the production of an unsaturated aldehyde and/or an unsaturated carboxylic acid. In the case where the raw material is propylene, the reaction bath temperature for determining Sn is set within the range where the propylene conversion is 90% to 99.9%.

As for the reaction bath temperature needed on the occasion of determining Sn, it is preferred to an actual temperature but not a set value. Similarly, an actual value is used for the hot spot temperature, too. In the measurement of the hot spot temperature, a thermocouple is placed in the gas flow direction within a reaction tube, the temperature is measured at intervals of about 5 cm to 10 cm, and a maximum temperature obtained within the catalyst layer is defined as the hot spot temperature. It is preferred that the interval of the temperature measurement is smaller. If the interval is larger than 10 cm, there may be the case where accurate data are not obtained, and hence, such is not preferred.

Production Method 1
(Preparation of Catalyst)

423.7 parts by weight of ammonium molybdate and 0.73 parts by weight of potassium nitrate were dissolved in 3,000 parts by weight of distilled water while heating and stirring, thereby obtaining an aqueous solution (A1). Separately, 378.4 parts by weight of cobalt nitrate, 139.6 parts by weight of nickel nitrate, and 161.6 parts by weight of ferric nitrate were dissolved in 1,000 parts by weight of distilled water, thereby preparing an aqueous solution (B1); and 97.1 parts by weight of bismuth nitrate was dissolved in 200 parts by weight of distilled water which had been made acidic by the addition of 81 parts by weight of concentrated nitric acid, thereby preparing an aqueous solution (C1). The above-described aqueous solution (A1) was mixed successively with (B1) and (C1) while vigorously stirring, and the produced liquid suspension was dried by using a spray dryer and preliminarily calcined at 440° C. for 6 hours, thereby obtaining a preliminarily calcined powder (D2). At that time, a formulation ratio of the catalytically active component exclusive of oxygen was Mo=12, Bi=1.0, Ni=3.0, Fe=2.0, Co=6.5, and K=0.05 in terms of an atomic ratio.

Thereafter, a powder of 100 parts by weight of the preliminarily calcined powder having 5 parts by weight of crystalline cellulose mixed therewith was added to an inert carrier (spherical substance containing alumina and silica as main components and having a diameter of 4.5 mm), and the carrier weight and the preliminarily calcined powder weight to be used for shaping were adjusted in a proportion such that the supporting rate defined according to the foregoing formula (2) accounted for 50% by weight. The mixture was supported and shaped in a spherical form having a diameter of 5.2 mm by using a 20% by weight glycerin solution as a binder, thereby obtaining a supported catalyst (E2). This supported catalyst (E2) was calcined in an air atmosphere at a calcination temperature of 530° C. for 4 hours, thereby obtaining a catalyst (F2). Similarly, the supported catalyst (E2) was calcined at a calcination temperature of 520° C. for 4 hours, thereby obtaining a catalyst (F3).

Similarly, a preliminarily calcined powder (D1) was obtained by using cesium nitrate in place of the potassium nitrate. A formulation ratio of the catalytically active component exclusive of oxygen of the resulting preliminarily calcined powder (D1) was Mo=12, Bi=1.0, Ni=3.0, Fe=2.0, Co=6.5, and Cs=0.03 in terms of an atomic ratio. This preliminarily calcined powder (D1) was supported and shaped in the same manner as that described above, thereby obtaining a supported catalyst (E1). This supported catalyst (E1) was calcined in an air atmosphere at a calcination temperature of 530° C. for 4 hours, thereby obtaining a catalyst (F1).

Comparative Production Example 1

423.7 parts by weight of ammonium molybdate and 1.64 parts by weight of potassium nitrate were dissolved in 3,000 parts by weight of distilled water while heating and stirring, thereby obtaining an aqueous solution (A2). Separately, 302.7 parts by weight of cobalt nitrate, 162.9 parts by weight of nickel nitrate, and 145.5 parts by weight of ferric nitrate were dissolved in 1,000 parts by weight of distilled water, thereby preparing an aqueous solution (B2); and 164.9 parts by weight of bismuth nitrate was dissolved in 200 parts by weight of distilled water which had been made acidic by the addition of 42 parts by weight of concentrated nitric acid, thereby preparing an aqueous solution (C2). The above-described aqueous solution (A2) was mixed successively with (B2) and (C2) while vigorously stirring, and the produced liquid suspension was dried by using a spray dryer and preliminarily calcined at 440° C. for 6 hours, thereby obtaining a preliminarily calcined powder (13). At that time, a formulation ratio of the catalytically active component exclusive of oxygen was Mo=12, Bi=1.7, Ni=2.8, Fe=1.8, Co=5.2, and K=0.15 in terms of an atomic ratio.

Thereafter, the preliminarily calcined powder (D3) was supported and shaped in the same manner as that in the preliminarily calcined powder (D2) in Production Example 1, thereby obtaining a supported catalyst (E3).

The supported catalyst (E3) was calcined in an air atmosphere at a calcination temperature of 530° C. for 4 hours, thereby obtaining a catalyst (F4).

In addition, the supported catalyst (E3) obtained in Comparative Production Example 1 was calcined in an air atmosphere at a calcination temperature of 520° C. for 4 hours, thereby obtaining a catalyst (F5).

Example 1

An oxidation reaction of propylene was carried out by using the catalysts (F1) to (F5) as prepared above, respectively. It is to be noted that though in this Example, the catalyst (F1) used on the raw material gas inlet side of the reaction tube and the catalyst (F2) or (F3) used on the raw material gas outlet side of the reaction tube are different in the formulation from each other, the both fall within the formulation range described in the formula (1).

A silica-alumina sphere having a diameter of 5.2 mm was filled in a length of 20 cm from the raw material gas inlet side of a stainless steel-made reactor having an inside diameter of 25 mm, in which a jacket for circulating a molten salt as a heat medium and a thermocouple for measuring the catalyst layer temperature were placed on a tube axis; a dilute catalyst prepared by mixing the catalyst (F1) and a silica-alumina mixture inert spherical carrier in a weight ratio of 85/15 in a length of 80 cm as an oxidation catalyst first layer (on the raw material gas inlet side), the catalyst (F1) in a length of 80 cm as an oxidation catalyst second layer, and the catalyst (F2) in a length of 190 cm as an oxidation catalyst third layer were successively filled, respectively toward the raw material gas outlet, thereby constituting the catalyst layer as a three-layer structure; and the reaction bath temperature was set to 330° C. Feed amounts of propylene, air, water, and nitrogen were set to a raw material molar ratio of propylene:oxygen:water:nitrogen=1:1.7:8.8:1; the gases were circulated such that a space velocity of propylene was 100 h$^{-1}$; and when the pressure on the reaction tube outlet side at the time of circulating all of the gases was set to 50 kPaG, and 300 hours elapsed after the start of reaction, the reaction bath temperature was varied to carry out the oxidation reaction of propylene. As values at the reaction bath temperature of 318° C. and 328° C., a hot spot temperature of the oxidation catalyst first layer and Sn and an effective yield of the same catalyst layer were obtained. The results are shown in Table 1. It is to be noted that a valued calculated by means of linear approximation was used as for Sn. In addition, as for the hot spot temperature in Table 1, a temperature at a hot spot exhibiting the maximum temperature among the hot spots in each of the catalyst layers was shown.

Example 2

The oxidation reaction of propylene was carried out in the same method as that in Example 1, except that under the oxidation reaction condition of Example 1, the oxidation catalyst (F3) was filled in a length of 190 cm as the oxidation catalyst third layer (on the gas outlet side). As values at the reaction bath temperature of 316° C. and 328° C., a hot spot temperature of the catalyst layer on the raw material gas inlet side and Sn and an effective yield of the same catalyst layer were obtained. The results are shown in Table 1.

Example 3

The oxidation reaction of propylene was carried out in the same method as that in Example 1, except that under the oxidation reaction condition of Example 1, the catalyst (F1) was filled in a length of 120 cm as the oxidation catalyst first layer (on the raw material gas inlet side), and the catalyst (F2) was successively filled in a length of 230 cm as the catalyst second layer (on the gas outlet side) toward the raw material gas outlet, thereby constituting the catalyst layer as a two-layer structure. As values at the reaction bath temperature of 314° C. and 324° C., a hot spot temperature of the catalyst layer on the raw material gas inlet side and Sn and an effective yield of the same catalyst layer were obtained. The results are shown in Table 1.

Example 4

The oxidation reaction of propylene was carried out in the same method as that in Example 1, except that under the oxidation reaction condition of Example 1, the catalyst (F1) was filled in a length of 135 cm as the oxidation catalyst first layer (on the raw material gas inlet side), and the oxidation catalyst (F2) was successively filled in a length of 165 cm as the catalyst second layer (on the gas outlet side) toward the raw material gas outlet, thereby constituting the catalyst layer as a two-layer structure; and that feed amounts of propylene, air, water, and nitrogen were set to a raw material molar ratio of propylene:oxygen:water:nitrogen=1:1.7:2:7.6, the gases were circulated such that a space velocity of propylene was 110 $h^{-1}$, and when the pressure on the reaction tube outlet side at the time of circulating all of the gases was set to 50 kPaG. As values at the reaction bath temperature of 310° C. and 321° C., a hot spot temperature of the catalyst layer on the raw material gas inlet side and Sn and an effective yield of the same catalyst layer were obtained. The results are shown in Table 1.

Example 5

The oxidation reaction of propylene was carried out in the same method as that in Example 4, except that under the oxidation reaction condition of Example 4, the gases were circulated such that a space velocity of propylene was 150 $h^{-1}$, and when the pressure on the reaction tube outlet side at the time of circulating all of the gases was set to 80 kPaG. As values at the reaction bath temperature of 314° C. and 326° C., a hot spot temperature of the catalyst layer on the raw material gas inlet side and Sn and an effective yield of the same catalyst layer were obtained. The results are shown in Table 1.

Comparative Example 1

The oxidation reaction of propylene was carried out in the same method as that in Example 1, except that under the oxidation reaction condition of Example 1, a dilute catalyst prepared by mixing the catalyst (F4) and a silica-alumina mixture inert spherical carrier in a weight ratio of 70/30 was filled in a length of 120 cm as the oxidation catalyst first layer (on the raw material gas inlet side), and the catalyst (F5) was successively filled in a length of 230 cm as the oxidation catalyst second layer (on the raw material gas inlet side) toward the raw material gas outlet, thereby constituting the catalyst layer as a two-layer structure; and that the gases were circulated such that a space velocity of propylene was 100 $h^{-1}$. As values at the reaction bath temperature of 322° C. and 330° C., a hot spot temperature of the catalyst layer on the raw material gas inlet side and Sn and an effective yield of the same catalyst layer were obtained. The results are shown in Table 1.

The results of the foregoing Examples and Comparative Example are summarized. In particular, it was noted that even in the case of largely varying the space velocity of propylene to 110 $h^{-1}$ to 150 $h^{-1}$ or the like as in Examples 4 and 5, Sn was kept low according to the method of the present invention.

As shown in Table 1, in comparison of Examples 1, 2 and 3 with Comparative Example 1, it was exhibited that according to the effects of the present invention, not only Sn (temperature sensitivity) can be reduced, but also the hot spot temperature itself relative to the reaction bath temperature can be decreased in combination with the effect of the catalyst species to be used. In addition, an effect for improving the yield could also be obtained at the same time due to a reduction of the hot spot.

TABLE 1

| | Space velocity of propylene ($h^{-1}$) | Reaction bath temperature (° C.) | Temperature of hot spot (° C.) | Sn | Maximum effective yield (mol %) |
|---|---|---|---|---|---|
| Example 1 | 100 | 328 | 401 | 2.05 | 91.8 |
| | | 318 | 380 | | |
| Example 2 | 100 | 328 | 397 | 2.21 | 91.3 |
| | | 316 | 370 | | |
| Example 3 | 100 | 324 | 407 | 1.20 | 91.5 |
| | | 314 | 395 | | |
| Example 4 | 110 | 321 | 394 | 1.86 | 91.1 |
| | | 310 | 376 | | |
| Example 5 | 150 | 326 | 406 | 2.02 | 90.1 |
| | | 314 | 383 | | |
| Comparative Example 1 | 100 | 330 | 419 | 7.73 | 91.1 |
| | | 322 | 353 | | |

While the invention has been described in detail and with reference to specific embodiments thereof, it will be apparent to one skilled in the art that various changes and modifications can be made therein without departing from the spirit and scope thereof.

It is to be noted that the present application is based on a Japanese patent application filed on Jul. 18, 2013 (Japanese Patent Application No. 2013-149333), the entireties of which are incorporated by reference. In addition, all references cited herein are incorporated as a whole.

INDUSTRIAL APPLICABILITY

The present invention is useful for the industrial plant of producing an unsaturated aldehyde or an unsaturated carboxylic acid.

The invention claimed is:

1. A method for producing an unsaturated aldehyde and/or an unsaturated carboxylic acid, which is a method for producing an unsaturated aldehyde and/or an unsaturated carboxylic acid each corresponding to an alkene by partially oxidizing the alkene using a fixed bed multitubular reactor,
wherein a plurality of catalyst layers formed by N division (N is N≥3) with respect to a gas flow direction of a reaction tube are provided, and
when a change (° C.) of hot spot temperature per 1° C. change of reaction bath temperature in the catalyst layer at the time of 300 hours elapsed after a start of the reaction and varying the reaction bath temperature is designated as Sn, at least one of the plurality of catalyst layers is regulated to Sn≤6,
in which the hot spot means a maximum value of the temperatures within the catalyst layers, and is a hot spot within the catalyst layer arranged nearest to a raw material gas inlet side or in the case where no maximum value of the temperatures is present in the catalyst layer arranged nearest to the raw material gas inlet side, a maximum value of the temperatures as a hot spot within the next or subsequent catalyst layer to the catalyst layer arranged nearest to the raw material gas inlet side, and
the reaction bath temperature for determining Sn is set within a range where an alkene conversion is 90% to 99.9%.

2. The method for producing an unsaturated aldehyde and/or an unsaturated carboxylic acid according to claim 1, wherein at least one of the plurality of catalyst layers is regulated to Sn≤3.

3. The method for producing an unsaturated aldehyde and/or an unsaturated carboxylic acid according to claim 1, wherein a concentration of the alkene in a raw material is 7 to 12% by volume.

4. The method for producing an unsaturated aldehyde and/or an unsaturated carboxylic acid according to claim 1, wherein all of the catalyst layers contain a complex metal oxide having a formulation represented by the following formula (1):

$$Mo_{12}Bi_aFe_bCo_cNi_dX_eY_fZ_gO_h \quad \text{Formula (1)}$$

X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), arsenic (As), antimony (Sb) and tungsten (W); Z is at least one element selected from the group consisting of sodium (Na), potassium (K), rubidium (Rb) and cesium (Cs); a to g represent atomic ratios of the respective components; h is a numerical value determined by degrees of oxidations of the catalyst components; a=0.80 to 2.0, b=1 to 3; c=3 to 7; d=2 to 4; e=0 to 10; f=0 to 10; g=0.01 to 0.10; h is expressed by the numerical value satisfying the oxidation states of other elements; d/a is 1.9 or more and 3.2 or less; d/g is 29 or more and 69 or less; and a/g is 18 or more and 39 or less.

5. The method for producing an unsaturated aldehyde and/or an unsaturated carboxylic acid according to claim 4, wherein b=1 to 2.5, d=2 to 3.5, and a/g is 18 or more and 35 or less.

6. A method for producing an unsaturated aldehyde and/or an unsaturated carboxylic acid, which is a method for producing an unsaturated aldehyde and/or an unsaturated carboxylic acid each corresponding to an alkene by partially oxidizing the alkene using a fixed bed multitubular reactor,
wherein a plurality of catalyst layers formed by N division (N is N=3) with respect to a gas flow direction of a reaction tube are provided, and
when a change (° C.) of hot spot temperature per 1° C. change of reaction bath temperature in the catalyst layer at the time of 300 hours elapsed after a start of the reaction and varying the reaction bath temperature is designated as Sn, at least one of the plurality of catalyst layers is regulated to Sn≤6,
in which the hot spot means a maximum value of the temperatures within the catalyst layers, and is a hot spot within the catalyst layer arranged nearest to a raw material gas inlet side or in the case where no maximum value of the temperatures is present in the catalyst layer arranged nearest to the raw material gas inlet side, a maximum value of the temperature as a hot spot within the next catalyst layer to the catalyst layer arranged nearest to the raw material gas inlet side, and
the reaction bath temperature for determining Sn is set within a range where an alkene conversion is 90% to 99.9%.

7. The method for producing an unsaturated aldehyde and/or an unsaturated carboxylic acid according to claim 6, wherein at least one of the plurality of catalyst layers is regulated to Sn≤3.

8. The method for producing an unsaturated aldehyde and/or an unsaturated carboxylic acid according to claim 6, wherein a concentration of the alkene in a raw material is 7 to 12% by volume.

9. The method for producing an unsaturated aldehyde and/or an unsaturated carboxylic acid according to claim 6, wherein all of the catalyst layers contain a complex metal oxide having a formulation represented by the following formula (1):

$$Mo_{12}Bi_aFe_bCo_cNi_dX_eY_fZ_gO_h \quad \text{Formula (1)}$$

X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), arsenic (As), antimony (Sb) and tungsten (W); Z is at least one element selected from the group consisting of sodium (Na), potassium (K), rubidium (Rb) and cesium (Cs); a to g represent atomic ratios of the respective components; h is a numerical value determined by degrees of oxidations of the catalyst components; a=0.80 to 2.0, b=1 to 3; c=3 to 7; d=2 to 4; e=0 to 10; f=0 to 10; g=0.01 to 0.10; h is expressed by the numerical value satisfying the oxidation states of other elements; d/a is 1.9 or more and 3.2 or less; d/g is 29 or more and 69 or less; and a/g is 18 or more and 39 or less.

10. The method for producing an unsaturated aldehyde and/or an unsaturated carboxylic acid according to claim 9, wherein b=1 to 2.5, d=2 to 3.5, and a/g is 18 or more and 35 or less.

11. A method for producing an unsaturated aldehyde and/or an unsaturated carboxylic acid, which is a method for producing an unsaturated aldehyde and/or an unsaturated carboxylic acid each corresponding to an alkene by partially oxidizing the alkene using a fixed bed multitubular reactor, wherein a plurality of catalyst layers formed by N division (N is N≥2) with respect to a gas flow direction of a reaction tube are provided, and when a change (° C.) of hot spot temperature per 1° C. change of reaction bath temperature in the catalyst layer at the time of 300 hours elapsed after a start of the reaction and varying the reaction bath temperature is designated as Sn, at least one of the plurality of catalyst layers is regulated to Sn≤6, in which the hot spot means a maximum value of the temperatures within the catalyst layers, and is a hot spot within the catalyst layer arranged nearest to a raw material gas inlet side, and the reaction bath temperature for determining Sn is set within a range where an alkene conversion is 90% to 99.9%.

12. The method for producing an unsaturated aldehyde and/or an unsaturated carboxylic acid according to claim 11, wherein at least one of the plurality of catalyst layers is regulated to Sn≤3.

13. The method for producing an unsaturated aldehyde and/or an unsaturated carboxylic acid according to claim 11, wherein a concentration of the alkene in a raw material is 7 to 12% by volume.

14. The method for producing an unsaturated aldehyde and/or an unsaturated carboxylic acid according to claim 11, wherein all of the catalyst layers contain a complex metal oxide having a formulation represented by the following formula (1):

$$Mo_{12}Bi_aFe_bCo_cNi_dX_eY_fZ_gO_h \qquad \text{Formula (1)}$$

X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), arsenic (As), antimony (Sb) and tungsten (W); Z is at least one element selected from the group consisting of sodium (Na), potassium (K), rubidium (Rb) and cesium (Cs); a to g represent atomic ratios of the respective components; h is a numerical value determined by degrees of oxidations of the catalyst components; a=0.80 to 2.0, b=1 to 3; c=3 to 7; d=2 to 4; e=0 to 10; f=0 to 10; g=0.01 to 0.10; h is expressed by the numerical value satisfying the oxidation states of other elements; d/a is 1.9 or more and 3.2 or less; d/g is 29 or more and 69 or less; and a/g is 18 or more and 39 or less.

15. The method for producing an unsaturated aldehyde and/or an unsaturated carboxylic acid according to claim 14, wherein b=1 to 2.5, d=2 to 3.5, and a/g is 18 or more and 35 or less.

* * * * *